United States Patent [19]
Azzolini et al.

[11] Patent Number: 5,461,928
[45] Date of Patent: Oct. 31, 1995

[54] DEVICE FOR COMPRESSING A SPECIMEN AT HIGH TEMPERATURE, IN PARTICULAR FOR ADVANCED TENSILE MATERIALS

[75] Inventors: Raymond Azzolini, St. Germain les Arpajon; Pierre Rochard, Orphin, both of France

[73] Assignee: Commissariat a l'Energie Atomique, Paris, France

[21] Appl. No.: 211,539
[22] PCT Filed: Oct. 14, 1992
[86] PCT No.: PCT/FR92/00968
  § 371 Date: Jun. 14, 1994
  § 102(e) Date: Jun. 14, 1994
[87] PCT Pub. No.: WO93/08456
  PCT Pub. Date: Apr. 29, 1993

[30] Foreign Application Priority Data
Oct. 15, 1991 [FR] France ................... 91 12686
[51] Int. Cl.⁶ .................................................. A01J 21/00
[52] U.S. Cl. ................ 73/818; 425/406; 100/258 R; 72/389
[58] Field of Search ............... 73/818, 821, 825, 73/856, 857; 425/78, 411, 406, 407, 408, 409, 412, 420; 100/258 R, 269 R, 236, 258 A; 72/455, 389, 465

[56] References Cited
U.S. PATENT DOCUMENTS

| 2,864,253 | 12/1958 | Lenton | 73/825 |
| 3,545,263 | 12/1970 | Hadley et al. | 73/825 |
| 3,975,950 | 8/1976 | Erdei | 73/825 |
| 4,599,215 | 7/1986 | Smarsly et al. | 425/78 |
| 5,272,904 | 12/1993 | Krumholz | 100/258 R |

Primary Examiner—Hezron E. Williams
Assistant Examiner—Richard A. Moller
Attorney, Agent, or Firm—Oblon, Spivak, McClelland, Maier & Neustadt

[57] ABSTRACT

A device for compressing a specimen which includes a fixed support assembly supporting the specimen and a mobile piston assembly which compresses the specimen. The support assembly and the piston assemblies have respective first and second planar faces in contact with and supporting the specimen. The specimen is compressed between the first and second planar faces. Each of the supported piston assembly include a swivel joint and a part of the mobile piston assembly has the first planar face slidably engaging a part of the fixed assembly having the second planar face.

6 Claims, 1 Drawing Sheet

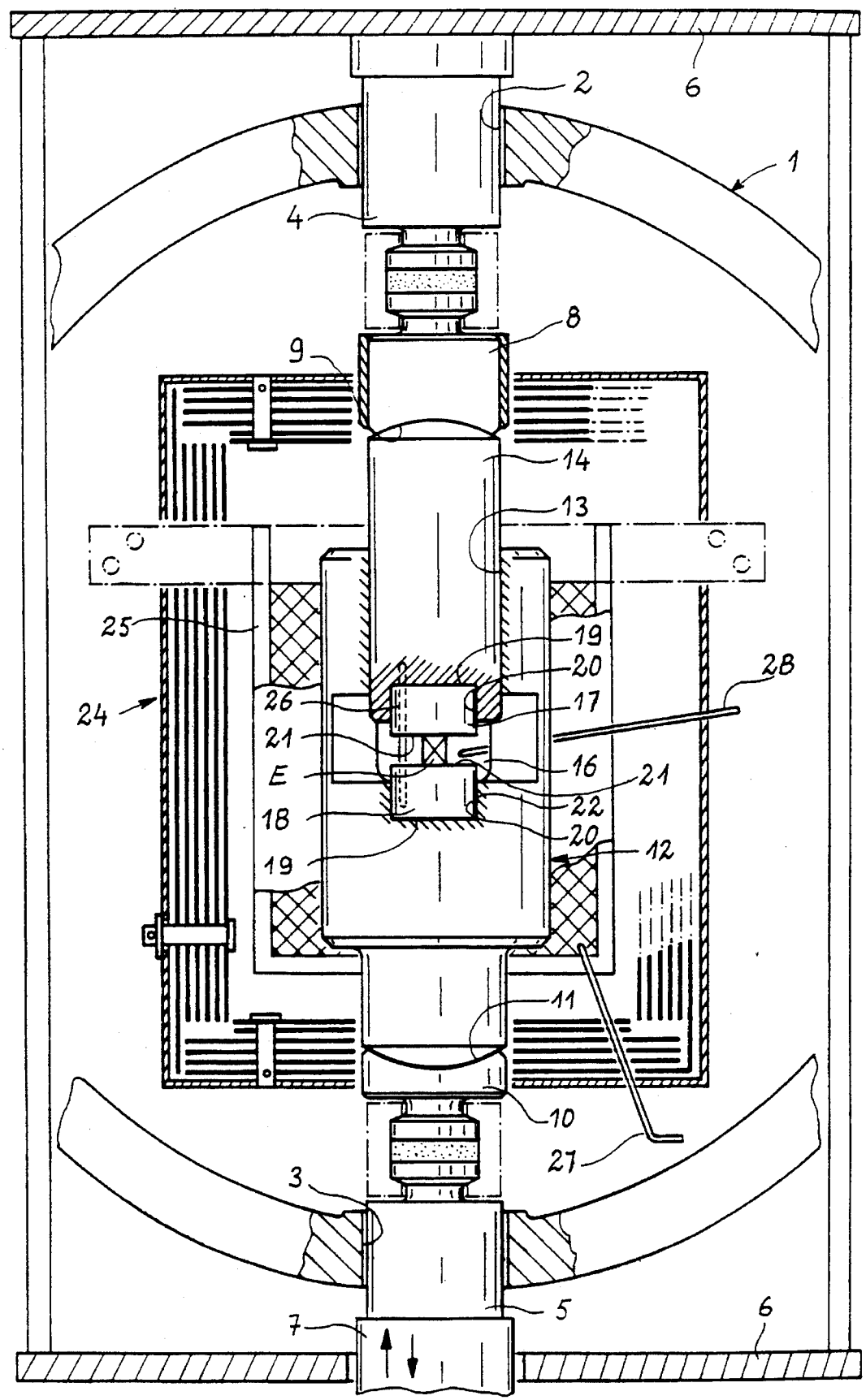

DEVICE FOR COMPRESSING A SPECIMEN AT HIGH TEMPERATURE, IN PARTICULAR FOR ADVANCED TENSILE MATERIALS

TECHNICAL FIELD

The invention relates to a compressing device ensuring a pure compression of a sample or specimen having two parallel faces between which it is compressed without any prior regulating operation of the press being necessary, even at high temperatures and for high loads.

BACKGROUND ART

Conventional mechanical testing machines used for such tests normally require difficult settings in order to obtain a strictly uniaxial stress, i.e. a pure and uniform compression on the specimen. They are generally constituted by two facing parts (by planar faces) and wherein one is a fixed support and the other a mobile piston. The sample is compressed by the advance of the piston, but long and difficult operations are necessary in order to reestablish a correct alignment of the two parts.

DISCLOSURE OF THE INVENTION

A satisfactory solution to this problem is offered by the invention, which is characterized in that the support and the piston are in each case constituted by two parts joined by a respective swivel joint, the parts which carry the planar faces being constructed so as to slide in one another.

Therefore said parts form an assembly which can be looked upon as a one-piece assembly, except in the testpiece compression direction. The double link by a swivel joint makes it possible to only transmit, in combination with the sliding bar adjustment, compressive stresses, despite all the deformations which may be caused by heat on the device.

The independence of the device with respect to the mechanical testing machine offers other advantages. It is easy to insert the device carrying the planar faces into a heating enclosure. These parts and the specimen are then heated to the desired test temperature, whereas the other parts which transmit the compressive force remain relatively cold.

The compression device is made from graphite with a low ash level (in order to prevent degassing at high temperature), because said material has good mechanical properties, which improve at high temperatures. However, the planar faces can advantageously belong to ceramic anvils, e.g. made from zirconia, in order to ensure a good mechanical strength at high temperatures.

BRIEF DESCRIPTION OF THE DRAWING

The single drawing illustrates an embodiment of the invention in a purely illustrative manner.

BEST MODE FOR CARRYING OUT THE INVENTION

The test machine comprises a furnace enclosure 1 formed from two cylindrical half-shells which close on one another and whereof only one is shown here. This half-shell has two diametrically opposite openings 2 and 3. A piston rod 4 fixed to a stationary frame 6 passes through one and a fixed support rod 5 through the other. The latter is fixed to a mobile jack 7 dependent on an electronic control system in order to compress a sample or specimen E. The piston 4 extends up to an end 8, whose free end face is in the form of a concave spherical cap 9. The support rod 5 also has an end 10 terminated by a free end face in the form of a concave spherical cap 11.

The support of the compressing device 12 is placed, without any prior setting, on the concave spherical cap 11 by a surface in the form of a convex spherical cap, which therefore forms a swivel joint with the spherical cap 11. It carries at its other end a bore 13 having a circular section in which slides the piston end 14 of the compression device, which has the same section and whose upper end is terminated by a convex spherical cap, which is partly fitted into the concave spherical cap 9 so as to form another swivel joint. There is only a very small clearance between the end of the piston 14 and the bore 13. An alignment error between the piston 14 and the fixed support rod 5 consequently leads to a different position of the support 12 and the end of the piston 14, but the force transmitted between these two parts remains parallel to the axis of the end of the piston 14.

The specimen support 12 is hollowed out to form a transverse depression 16 into which issues the bore 13. Into depression 16 it is introduced the specimen E. It is in reality compressed between two zirconia anvils 17 and 18, which respectively form part of the end of the piston 14 and the support 12. Each of the anvils 17 and 18 is more specifically a short cylinder, whereof a rear, planar face 19 bears on the planar, bottom surface of a blind hole 20 with the same section and formed at the end of the piston 14 and in the sample support 12, and a front, planar face 21 used for supporting the sample E and compressing the sample between two, parallel front faces 21 of the sample. Finally, a circular, lateral surface 22 of the anvils 17 and 18 is fitted in the side wall of the blind holes 20.

The heating device is constituted by a thermal insulation shield 24 and two half-resistors 25 responsible for heating. The thermal insulation shield 24 makes it possible to confine the compression device in a heating zone constituted by two half-resistors 25, both connected to the two half-shells of the furnace enclosure 1. The adopted configuration makes it possible to raise the compression device (piston 14, support 12 and anvils 17,18) to the same temperature as the specimen E, whereas the support rod 5 and the piston 4 remain at a virtually invariable temperature. The heating device is provided with a thermocouple 27 permitting the regulation of the temperature and a thermocouple 28 measuring the temperature on the specimen E.

The compression device makes it possible to measure deformations of the sample throughout a test. Its shape (transverse depression 16 of the support 12 and the anvils 17,18) appropriate for a contact-free extensometry by means of a laser permits the measurement of the following quantities of the material tested at high temperature (Young's modulus, expansion coefficient, elastic and plastic deformations). The measurement takes place through a slot 26 made in the heat shield 24.

The compression device is able to stress ceramic specimens up to 2200° C. in a vacuum or a controlled atmosphere, and carbon-containing products up to 3000° C. under a controlled atmosphere. The loads which can be reached are e.g. 100,000 N at 1500° C.

We claim:

1. A device for compressing a specimen (E), which comprises:

a fixed support assembly (4,14,17) supporting the specimen and a mobile piston assembly (7,12,18) compressing the specimen, the support assembly and piston assemblies respectively having first and second planar faces (21,21) in contact with and supporting the specimen, the specimen being compressed between the first and second planar faces (21,21) wherein the support and piston assemblies each comprise a swivel joint (9,11), and wherein a part of the mobile piston assembly having the first planar face (21) slidably engages a part of the fixed support assembly having the second planar face (21).

2. The device according to claim 1, which comprises a heating enclosure (24) enveloping a part of each of the support and piston assemblies having the first and second planar faces (21, 22).

3. The device according to claim 1, wherein the first and second planar faces each comprise zirconia.

4. The device according to claim 3, wherein each of the first and second planar faces comprise planar faces of an anvil (17,18).

5. The device according to claim 3, which comprises a heating enclosure (24) enveloping a part of each of the support assembly and piston assemblies having the first and second planar faces (21,21).

6. The device according to claim 5, wherein each of the first and second planar faces comprise planar faces of an anvil (17,18).

* * * * *